US009044531B2

(12) United States Patent
Dave et al.

(10) Patent No.: US 9,044,531 B2
(45) Date of Patent: Jun. 2, 2015

(54) VASCULAR CLOSURE DEVICE

(71) Applicant: Cordis Corporation, Fremont, CA (US)

(72) Inventors: Vipul Bhupendra Dave, Hillsborough, NJ (US); Chao Chin-Chen, Edison, NJ (US)

(73) Assignee: Cordis Corporation, Fremont, CA (US)

( * ) Notice: Subject to any disclaimer, the term of this patent is extended or adjusted under 35 U.S.C. 154(b) by 0 days.

(21) Appl. No.: 14/337,776

(22) Filed: Jul. 22, 2014

(65) Prior Publication Data

US 2014/0336700 A1 Nov. 13, 2014

Related U.S. Application Data

(62) Division of application No. 12/261,570, filed on Oct. 30, 2008, now Pat. No. 8,790,684.

(60) Provisional application No. 60/984,282, filed on Oct. 31, 2007.

(51) Int. Cl.
| | |
|---|---|
| A61F 2/02 | (2006.01) |
| A61B 17/03 | (2006.01) |
| A61L 31/16 | (2006.01) |
| A61B 17/00 | (2006.01) |
| A61L 31/14 | (2006.01) |

(52) U.S. Cl.
CPC ............. *A61L 31/16* (2013.01); *A61B 17/0057* (2013.01); *A61L 31/141* (2013.01); *A61B 2017/00004* (2013.01)

(58) Field of Classification Search
None
See application file for complete search history.

(56) References Cited

U.S. PATENT DOCUMENTS

| | | | |
|---|---|---|---|
| 3,068,864 A | 12/1962 | Tietze | |
| 3,629,477 A | 12/1971 | Model et al. | |
| 3,767,362 A | 10/1973 | Griffin et al. | |
| 3,815,315 A | 6/1974 | Glick | |
| 3,839,297 A | 10/1974 | Wasserman et al. | |
| 3,929,992 A | 12/1975 | Sehgal et al. | |
| 4,027,676 A | 6/1977 | Mattei | |
| 4,105,034 A | 8/1978 | Shalaby et al. | |
| 4,126,221 A | 11/1978 | Cerwin | |
| 4,185,637 A | 1/1980 | Mattei | |
| 4,201,216 A | 5/1980 | Mattei | |
| 5,128,101 A | 7/1992 | Boynton | |
| 5,230,424 A | 7/1993 | Alpern et al. | |
| 5,464,580 A | 11/1995 | Popescu et al. | |
| 5,555,976 A | 9/1996 | Pernot | |
| 5,868,244 A | 2/1999 | Ivanov et al. | |
| 5,972,008 A | 10/1999 | Kalinski et al. | |
| 5,980,927 A | 11/1999 | Nelson et al. | |
| 6,090,130 A | 7/2000 | Nash et al. | |
| 6,179,863 B1 | 1/2001 | Kensey et al. | |
| 6,190,407 B1 | 2/2001 | Ogle et al. | |
| 6,260,699 B1 | 7/2001 | Kaplan et al. | |
| 6,514,517 B2 | 2/2003 | Jamiolkowski et al. | |
| 6,881,766 B2 | 4/2005 | Hain | |
| 6,969,397 B2 | 11/2005 | Ginn | |
| 7,083,644 B1 | 8/2006 | Moroni | |
| 2004/0127978 A1 | 7/2004 | Sparer et al. | |
| 2005/0119562 A1* | 6/2005 | Jones et al. | ............ 600/426 |
| 2005/0267521 A1 | 12/2005 | Forsberg | |
| 2005/0267528 A1 | 12/2005 | Ginn et al. | |
| 2006/0021212 A1* | 2/2006 | Wang et al. | ............ 29/596 |
| 2006/0052822 A1 | 3/2006 | Mirizzi et al. | |
| 2006/0058844 A1 | 3/2006 | White et al. | |
| 2006/0212127 A1 | 9/2006 | Karabey et al. | |
| 2006/0265007 A1 | 11/2006 | White et al. | |
| 2007/0032823 A1 | 2/2007 | Tegg | |
| 2007/0032824 A1 | 2/2007 | Terwey | |
| 2007/0073345 A1 | 3/2007 | Pipenhagen et al. | |
| 2007/0123816 A1 | 5/2007 | Zhu et al. | |
| 2007/0232169 A1 | 10/2007 | Strickler et al. | |

FOREIGN PATENT DOCUMENTS

| | | |
|---|---|---|
| CA | 2 495 181 A1 | 2/2004 |
| CA | 2657536 A1 | 11/2007 |
| EP | 0761243 A1 | 3/1997 |
| WO | WO 2004/014448 A1 | 2/2004 |
| WO | WO 2004/032704 A1 | 4/2004 |
| WO | WO 2007/121747 A1 | 11/2007 |
| WO | WO 2007121747 A1 * | 11/2007 |

OTHER PUBLICATIONS

Canadian Examiner's Report dated Feb. 29, 2012 in corresponding Canadian Application No. 2,703,953.
Office Action, mailed Jun. Jun. 23, 2011, in related U.S. Appl. No. 12/261,620.
International Search Report for corresponding US Appln. No. PCT/US2008/081770, mailed Feb. 23, 2010.
International Search Report for corresponding US Appln. No. PCT/US2008/081867, mailed Feb. 23, 2010.
Bhargava, H. et al., "Tricloson: Applications and Safety", American J. Infectious Control, vol. 24, pp. 209-218 (1996).
Encyclopedia of Polymer Science and Engineering, "Nomenclature", (1987) vol. 10, pp. 204-253.

\* cited by examiner

*Primary Examiner* — H. Sarah Park

(57) ABSTRACT

A biocompatible material may be configured into any number of implantable medical devices including a vascular closure device. The vascular closure device includes a fibrous structure formed from at least one randomly oriented fiber, the randomly oriented fiber comprising at least one polymer, and at least one agent, in therapeutic dosage, incorporated into at least one of the fibrous structure and the at least one randomly oriented fiber.

4 Claims, 8 Drawing Sheets

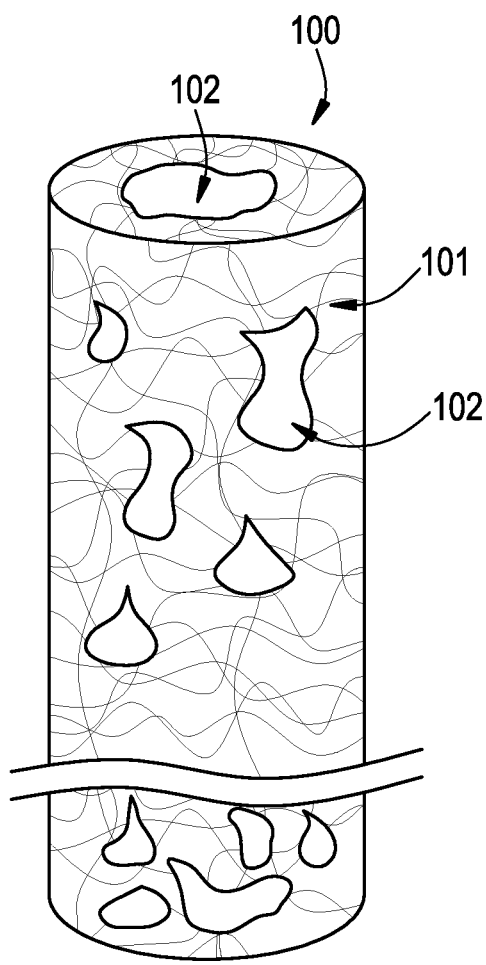
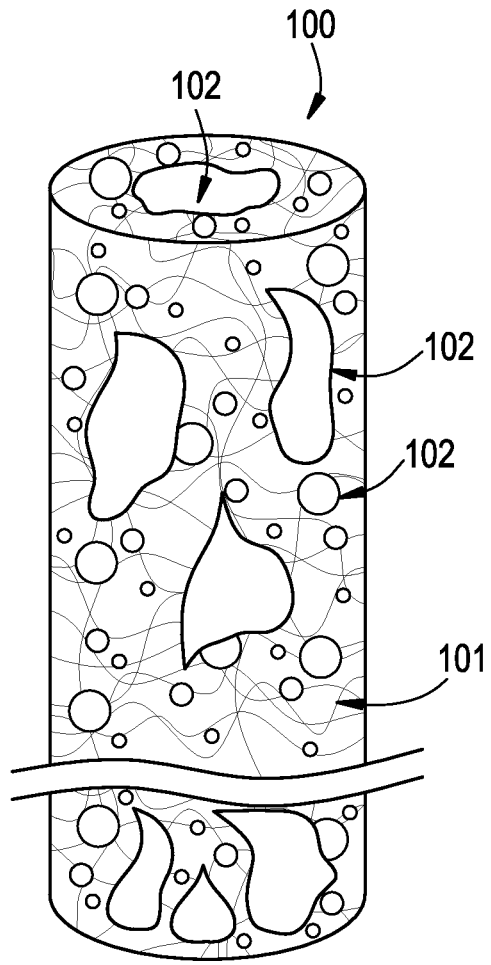

VASCULAR CLOSURE DEVICE

PRIORITY

This application is a divisional application under 35USC§§120 and 121 of U.S. patent application Ser. No. 12/261,570 filed on Oct. 30, 2008 (now allowed), which claims the benefit of U.S. Provisional Application Ser. No. 60/984,282, filed Oct. 31, 2007 under applicable sections of 35 USC §119, all of the prior applications are hereby incorporated by reference in their entireties into this application.

BACKGROUND OF THE INVENTION

1. Field of the Invention

The present invention relates to vascular closure devices, and more particularly to vascular closure devices formed from bioabsorbable polymers and structures, blends of bioabsorbable polymers and plasticizers, blends of polymers, plasticizers, antibacterial agents and therapeutic agents, or any combination thereof. These polymeric closure devices may be prepared by different processes.

2. Discussion of the Related Art

Each year, patients undergo a vast number of surgical procedures in the United States. Current data shows about twenty-seven million procedures are performed per year. Post operative or surgical site infections ("SSIs") occur in approximately two to three percent of all cases. This amounts to more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the cost of treatment to patients.

From a clinical perspective, it is generally necessary to administer a chemical compound that will provide anti-biotic or anti-bacterial, anti-fungal, or anti-parasitical activity when a vascular closure device is used in high-risk patients (e.g., prior MI, stroke, diabetes, or additional risk factors). Most infections associated with medical device are caused by bacteria. The primary mode of infection associated with medical device is attachment of microorganisms to the device followed by growth and formation of a biofilm on the device. Once a biofilm is formed, it is practically impossible to treat the infection without actually removing the device.

Implantable medical devices that contain antimicrobial agents applied to or incorporated within have been disclosed and/or exemplified in the art. Examples of such devices are disclosed in European Patent Application No. EP 0761243. Actual devices exemplified in the application include French Percuflex catheters. The catheters were dip-coated in a coating bath containing 2,4,4'-tricloro-2-hydroxydiphenyl ether [Ciba Geigy Irgasan; (DP300)] and other additives. The catheters were then sterilized with ethylene oxide and stored for thirty days. Catheters coated with such solutions exhibited antimicrobial properties, i.e., they produced a zone of inhibition when placed in a growth medium and challenged with microorganism, for thirty days after being coated.

There have been efforts to prepare antibacterial surgical devices such as sutures as disclosed in U.S. Pat. No. 6,514,517 B2 (Antibacterial Coatings for Medical Devices); U.S. Pat. No. 6,881,766 B2 (Sutures and Coatings Made from Therapeutic Absorbable Glass) and WO 2004/032704 A2 (Packaged Antimicrobial Medical Device and Method of Preparing Same).

There have been several closure devices disclosed in prior art as described in U.S. Pat. No. 6,090,130 (Hemostatic puncture closure system including blood vessel locator and method of use) and U.S. Pat. No. 6,179,863 B1 (Hemostatic puncture closure system and method of use) by Kensey Nash Corporation; US 2007/0073345 A1 (Vascular sealing device with high surface area sealing plug), US 2007/0032824 A1 (Tissue puncture closure device with track plug), US 2007/0032823 A1 (Tissue puncture closure device with coiled automatic tamping system), US 2006/0265007 A1 (Tissue puncture closure system with retractable sheath), US 2006/0058844 A1 (Vascular sealing device with locking system) and US 2005/0267521 A1 (Collagen sponge for arterial sealing) by St. Jude Medical; and U.S. Pat. No. 6,969,397 (Guide wire element for positioning vascular closure devices and method for use) and US 2005/0267528 A1 (Vascular plug having composite construction) by Ensure Medical. In these disclosures, bioabsorbable plugs were used for puncture closure.

Most implantable medical devices are manufactured, sterilized and contained in packages until opened for use in a surgical procedure. During surgery, the opened package containing the medical device, packaging components contained therein, and the medical device, is exposed to the operating room atmosphere, where bacteria from the air may be introduced. Incorporating antimicrobial properties into the closure plug delivery system, package and/or the packaging components contained therein substantially prevents bacterial colonization on the package and components once the package has been opened. The antimicrobial package and/or packaging components in combination with the incorporation of antimicrobial properties onto or into the medical device itself would substantially ensure an antimicrobial environment about the sterilized medical device.

SUMMARY OF THE INVENTION

The present invention relates to an implantable medical device, and in particular, a bioabsorbable vascular closure medical device that may include therapeutic agent(s) and methods for preparing such medical devices. In accordance with embodiments of the present invention, an agent is disposed on the surfaces, in interstitial spaces, and/or in the bulk of the medical device.

In one embodiment of the invention, the implantable medical device comprises a fibrous structure configured for sealing a wound. The fibrous structure is formed from at least one randomly oriented fiber formed from at least one polymer. At least one agent, in therapeutic dosage, may be incorporated into at least one of the fibrous structure and the at least one randomly oriented fiber, and configured for controlled elution therefrom.

Another embodiment of the vascular closure medical device includes an antimicrobial agent disposed thereon, the antimicrobial agent being selected from halogenated hydroxyl ethers, acyloxydiphenyl ethers, and combinations thereof, silver containing compounds, chlorhexidine gluconate, methylisothiazolone, terpineol, thymol, chloroxylenol, cetylpyridinium chloride, iodine compounds, chlorinated phenols, quaternary ammonium compounds, biguanide compounds, and gentian violet compounds. The amount is sufficient to substantially inhibit bacterial colonization on the medical device.

The present invention is also directed to applying and utilizing vascular closure devices to minimize the potential for infection at the puncture site.

In accordance with one aspect, the present invention is directed to an implantable medical device which comprises a structure formed from at least one polymer, and at least one therapeutic agent or antimicrobial agent dispersed throughout the at least one polymer.

In accordance with another aspect, the present invention is directed to an implantable medical device which comprises a structure formed from a first material, and a coating layer affixed to the first material, the coating layer including at least one therapeutic agent or antimicrobial agent dispersed throughout a polymeric material.

In accordance with another aspect, the present invention is directed to an implantable medical device which comprises a fibrous structure formed from at least one polymer, and at least one therapeutic agent or antimicrobial agent dispersed throughout the at least one polymer.

In accordance with another aspect, the present invention is directed to an implantable medical device which comprises a porous vascular closure device formed from at least one polymer, and at least one therapeutic agent or antimicrobial agent dispersed throughout the at least one polymer.

The implantable medical devices of the present invention may be formed out of any number of biocompatible polymeric materials. In order to achieve the desired properties, the polymeric material, whether in the raw state or in the tubular or sheet or fibrous or porous state may be physically deformed to achieve a certain degree of alignment of the polymer chains.

The medical devices of the present invention may also be formed from blends of polymeric materials, blends of polymeric materials and plasticizers, blends of polymeric materials and therapeutic agents, blends of polymeric materials and antimicrobial agents, blends of polymeric materials with both therapeutic and antimicrobial agents, blends of polymeric materials with plasticizers and therapeutic agents, blends of polymeric materials with plasticizers and antimicrobial agents, blends of polymeric materials with plasticizers, therapeutic agents and antimicrobial agents, and/or any combination thereof. By blending materials with different properties, a resultant material may have the beneficial characteristics of each independent material. In addition, by blending either or both therapeutic agents and antimicrobial agents together with the other materials, higher concentrations of these materials may be achieved as well as a more homogeneous dispersion. Various methods for producing these blends include solvent and melt processes and coating techniques.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 6C illustrates a plug that has been dip coated with a agent/solvent solution according to one embodiment of the present invention.

FIG. 6D illustrates a plug having agent occupying the interstitial spaces that has been dip coated with a agent/solvent solution according to one embodiment of the present invention.

DETAILED DESCRIPTION OF THE PREFERRED EMBODIMENTS

Figure 1:
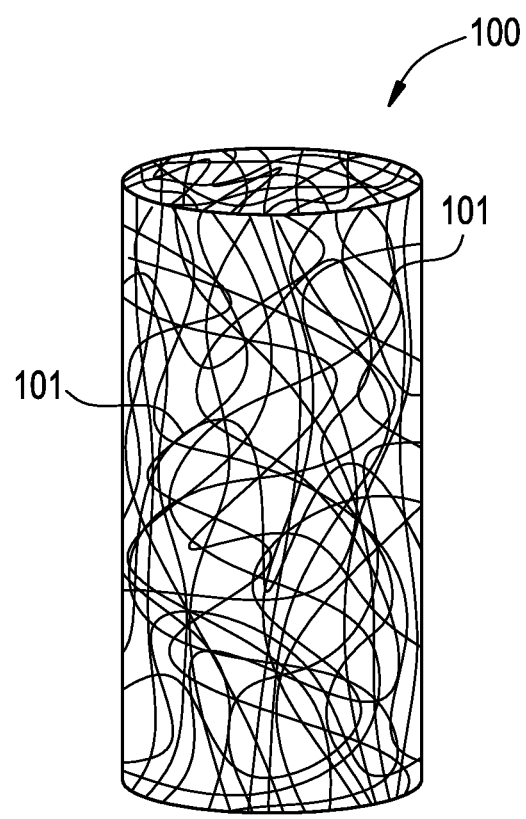
FIG. 1 is an isometric view of a fibrous antimicrobial plug according to one embodiment of the present invention.

Implantable medical devices may be fabricated from any number of suitable biocompatible materials, including polymeric materials. The internal structure of these polymeric materials may be altered utilizing mechanical and/or chemical manipulation of the polymers. These internal structure modifications may be utilized to create devices having specific gross characteristics such as crystalline and amorphous morphology and orientation as is explained in detail subsequently. Although the present invention applies to any number of implantable medical devices, for ease of explanation, the following detailed description will focus on an exemplary vascular closure device.

In accordance with the present invention, implantable medical devices may be fabricated from any number of biocompatible materials, including polymeric materials. These polymeric materials may be non-degradable, biodegradable and/or bioabsorbable. These polymeric materials may be formed from single polymers, blends of polymers and blends of polymers and plasticizers. In addition, other agents such as drugs and/or antimicrobial agents may be blended with the materials described above or affixed or otherwise added thereto. A number of chemical and/or physical processes may be utilized to alter the chemical and physical properties of the materials and ultimately the final devices.

Exemplary Devices

Catheterization and interventional procedures, such as angioplasty and stenting, generally are performed by inserting a hollow needle through a patient's skin and muscle tissue into the vascular system. This creates a puncture wound in a blood vessel, frequently the femoral artery, which, once the interventional procedure has been completed, needs to be closed or sealed in a suitable manner.

Procedures and devices have been proposed for accomplishing such closure which involve the use of an introducer sheath that is placed in the tract of the puncture wound following which a closure delivering device is introduced through the introducer sheath to deploy a sealing or closing element within the tract. The vascular closure device in one embodiment of the present invention is one such device. The vascular closure device substantially occludes blood flow from a puncture.

In a preferred embodiment, the vascular closure device is a porous plug preferably prepared from a bioabsorbable material. There are several approaches that can be used to make these plugs with antibacterial additives.

It is generally known to use multilayered fabrics in connection with medical procedures. For example, multilayered fabrics are used as all purpose pads, wound dressings, surgical meshes, including hernia repair meshes, adhesion prevention meshes and tissue reinforcement meshes, defect closure devices, and hemostats. Additionally, multilayered fabrics are useful for tissue engineering and orthopedic applications. The recent emergence of tissue engineering offers numerous approaches to repair and regenerate damaged/diseased tissue. Tissue engineering strategies have explored the use of biomaterials that ultimately can restore or improve tissue function. The use of colonizable and remodelable scaffolding materials has been studied extensively as tissue templates, conduits, barriers and reservoirs. In particular, synthetic and natural materials in the form of foams, sponges, gels, hydrogels, textiles, and nonwovens have been used in vitro and in vivo to reconstruct/regenerate biological tissue, as well as deliver agents for inducing tissue growth. The different forms of scaffolds may be laminated to form a multilayered tissue engineering scaffold.

As used herein, the term "nonwoven fabric" includes, but is not limited to, bonded fabrics, formed fabrics, or engineered fabrics, that are manufactured by processes other than spinning, weaving or knitting. More specifically, the term "nonwoven fabric" refers to a porous, textile-like material, usually in flat sheet form, composed primarily or entirely of staple fibers assembled in a web, sheet or bats. The structure of the nonwoven fabric is based on the arrangement of, for example, staple fibers that are typically arranged more or less randomly. The tensile stress-strain and tactile properties of the nonwoven fabric ordinarily stem from fiber to fiber friction created by entanglement and reinforcement of, for example, staple fibers, and/or from adhesive, chemical or physical bonding. Notwithstanding, the raw materials used to manufacture the nonwoven fabric may be yarns, scrims, netting, or filaments made by processes that include spinning, weaving or knitting.

Preferably, the nonwoven fabric is made by processes other than spinning, weaving or knitting. For example, the nonwoven fabric may be prepared from yarn, scrims, netting or filaments that have been made by processes that include spinning, weaving or knitting. The yarn, scrims, netting and/or filaments are crimped to enhance entanglement with each other and attachment to the second absorbable woven or knitted fabric. Such crimped yarn, scrims, netting and/or filaments may then be cut into staple that is long enough to entangle. The staple may be between about 0.1 and 3.0 inches long, preferably between about 0.75 and 2.5 inches, and most preferably between about 1.5 and 2.0 inches. The staple may be carded to create a nonwoven bat, which may be then needle-punched or calendared into an absorbable nonwoven fabric. Additionally, the staple may be kinked or piled.

Figure 4A:
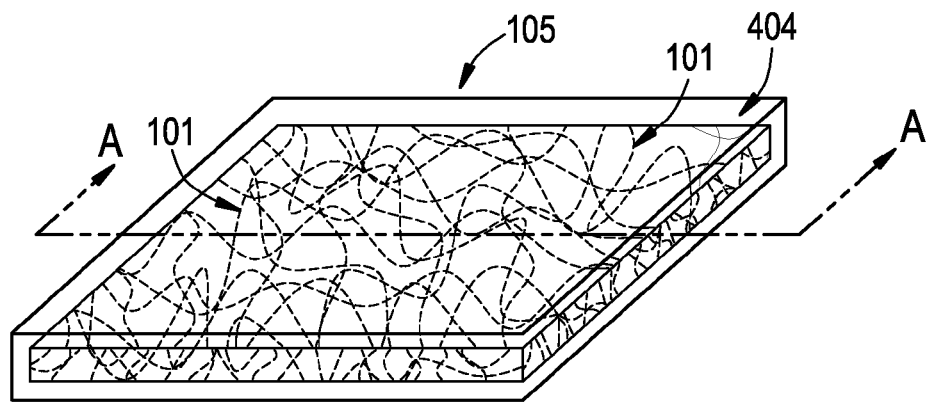
FIG. 4A is a schematic representation of a non-woven fibrous mat according to one embodiment of the present invention.

FIG. 4A is a schematic representation of a non-woven fibrous mat according to one embodiment of the present invention. The non-woven mat 105 is formed from filaments or fibers 101 entangled in random order. In a preferred embodiment, the non-woven mat 105 also includes an antibacterial or antimicrobial agent 102 dispersed throughout the mat, either in, on or between the entangled fibrous structure.

Other methods known for the production of nonwoven fabrics may be utilized and include such processes as air laying, wet forming and stitch bonding. Such procedures are generally discussed in the Encyclopedia of Polymer Science and Engineering, Vol. 10, pp. 204-253 (1987) and Introduction to Nonwovens by Albin Turbak (Tappi Press, Atlanta Ga. 1999), both incorporated herein in their entirety by reference.

The thickness of the nonwoven fabric may range from about 0.25 to 2 mm. The basis weight of the nonwoven fabric ranges from about 0.01 to 0.2 $g/in^2$; preferably from about 0.03 to 0.1 $g/in^2$; and most preferably from about 0.04 to 0.08 $g/in^2$.

Additionally, the nonwoven fabric may comprise pharmacologically and biologically active agents, including but not limited to, wound healing agents, antibacterial agents, antimicrobial agents, growth factors, analgesic and anesthetic agents. When used as a tissue scaffold, the reinforced absorbable multilayer fabric may be seeded or cultured with appropriate cell types prior to implantation for the targeted tissue.

A typical process to make the vascular closure plug according to one embodiment of the present invention is as follows:

The desired absorbable polymer resin [e.g., poly(glycolic acid)] is melt extruded in to multi-filaments (about 40 to 70 filaments) with different denier (about 120 to 150 denier) and tenacity (about 3 to 7 grams/denier). During the melt spinning process, a spin finish is applied on the fiber surface to prevent excessive fiber breakage. The fibers are then crimped and cut in to short staple fibers (for example, 1-2 inches staple lengths), carded and needle punched to prepare a non-woven mat with the desired density and integrity. The mat is rinsed (scoured) with a solvent (e.g., isopropanol or acetone or hexane, ethyl acetate or other co-solvents) to remove the spin finish and dried; and then cut in to cylindrical plugs or other desired geometry.

FIG. 1 is an isometric view schematically representing a fibrous antimicrobial plug according to one embodiment of the present invention. The plug 100 includes randomly oriented fiber or fibers 101. In a preferred embodiment the plug 100 may also include an agent, preferably an antibacterial or antimicrobial agent on, within or in between the fibers 101. In addition the agent may be coated over the entire plug 100.

The antibacterial (or any other agents) is added by different ways in the above-mentioned manufacturing process as described below in further details.

Figure 2A:
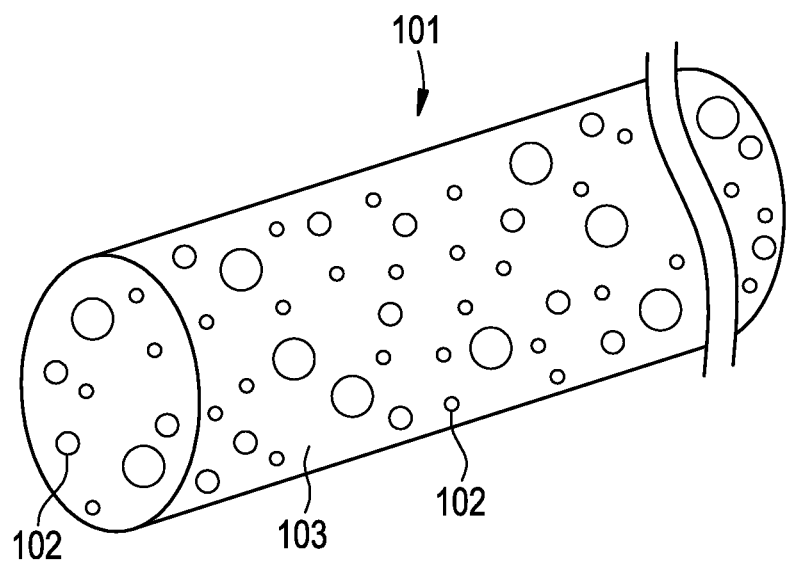
FIG. 2A is a schematic representation of a fiber in the vascular closure plug showing the dispersion of the antimicrobial agent within the individual fiber structure according to one embodiment of the present invention.
Figure 2B:
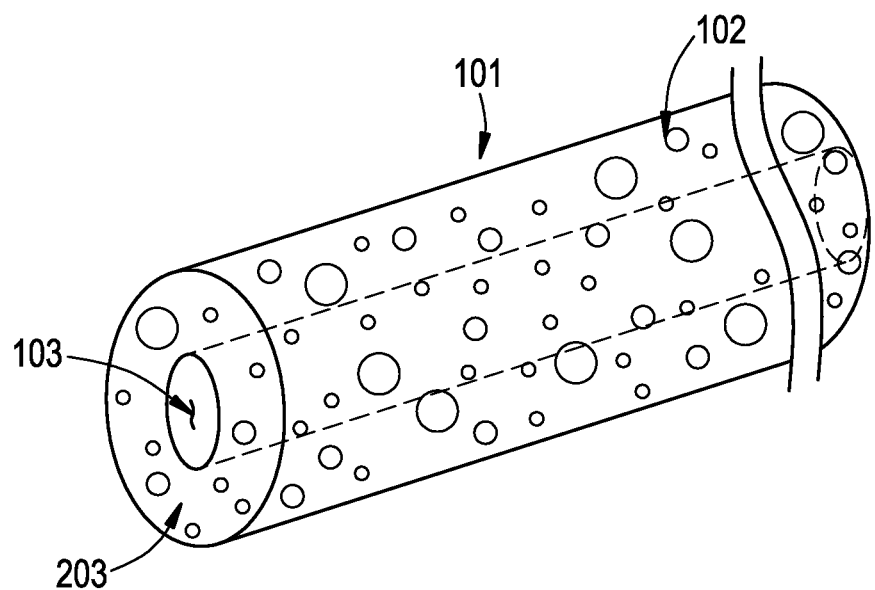
FIG. 2B is a schematic representation of a fiber in the vascular closure plug showing the dispersion of the antimicrobial agent within the outer polymer layer of the fiber structure according to one embodiment of the present invention.

In one embodiment of the invention, the agent may be added (bulk loaded) in the fiber matrix during the melt spinning process. FIG. 2A shows the dispersion of the antimicrobial agent in the fiber matrix forming the plug 100 according to one embodiment of the present invention. The bulk loaded fiber 101 is comprised of an agent 102 dispersed within a polymer 103. One way this is achieved is by preparing a master batch concentrate of the agent 102 and then adding desired amount of the concentrate to the polymer 103 during the fiber extrusion process. This allows uniform dispersion of large quantity of the agent 102 in the fiber 101 and provides long-term diffusion of the agent 102 during the life cycle of the plug 100 in the vascular environment. The agent 102 is preferably thermally stable at melt processing temperatures. Alternatively, the agent 102 can be added on, or incorporated into a polymeric layer on the fiber 101 surfaces. FIG. 2B is a schematic representation of a fiber in the plug 100 showing the dispersion of the agent within the outer polymer layer of the fiber structure according to one embodiment of the present invention. This type of fiber 101 may be formed by mixing the agent 102 with a low melting polymer 203 (e.g., Polycaprolactone/Polyglycolic acid copolymer) to form a sheath on the core fiber (filament) 103 (e.g., PGA) using a bicomponent fiber spinning technology. Referring again to FIG. 2B, the antimicrobial agent 102 is dispersed within polymer layer 203, which is coated on the base polymer 103. Together, this bicomponent fiber 101 forms the fibrous structure of the plug 100.

Figure 3:
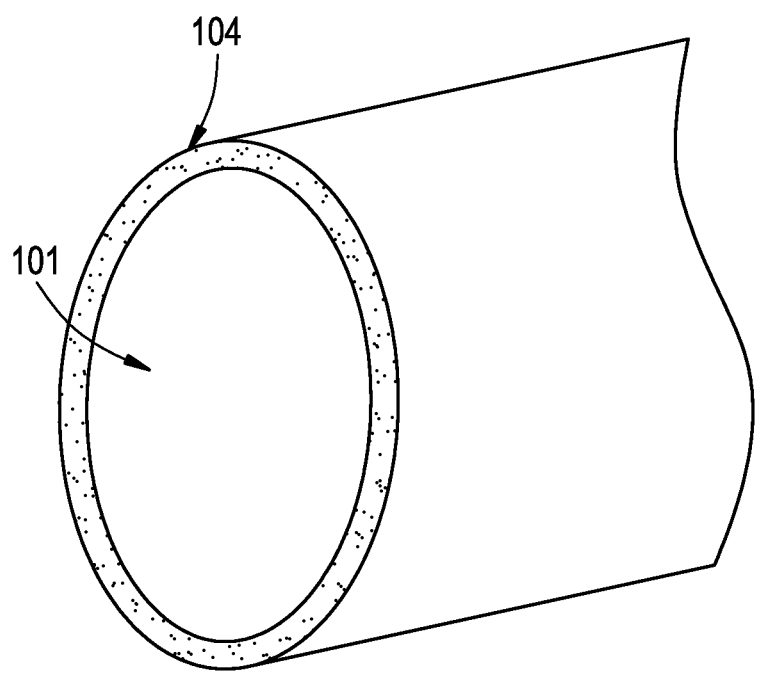
FIG. 3 is a schematic representation of the fiber in the vascular closure plug having a thin coating of spin finish/lubricant plus agent along the outer surface of the fiber structure according to one embodiment of the present invention.

In accordance with another embodiment of the invention, the agent 102 may be mixed with the spin finish that is coated during the melt spinning process. This approach allows the agent 102 to disperse uniformly on the fiber 101 surfaces. FIG. 3 is a schematic representation of the fiber 101 comprising the plug 100 having a thin coating 104 along the outer surface of the fibrous structure 101. The scouring process should not be used to remove the surface coatings when using this approach. Accordingly, the thin outer coating 104 comprises the spin finish/lubricant plus the agent 102.

Figure 4B:
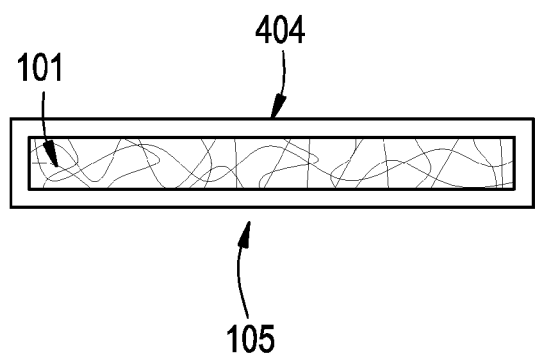
FIG. 4B is a section view of the non-woven mat depicted in FIG. 4A taken along reference line A-A.
Figure 4C:
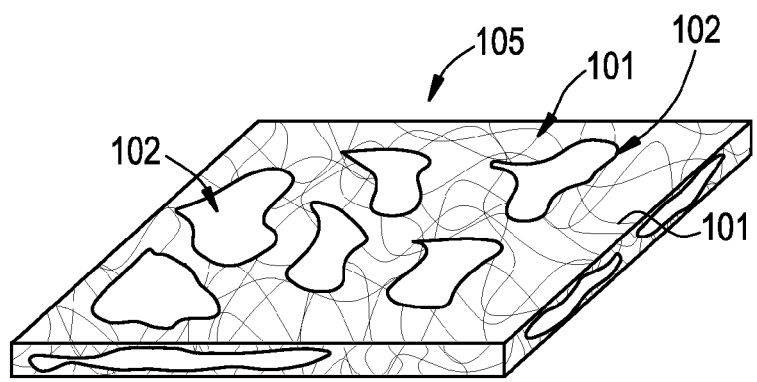
FIG. 4C is a schematic representation of a non-woven fibrous mat according to one embodiment of the present invention.

In another embodiment of the invention, the agent may be dip coated on the scoured non-woven mat 105, which is then cut into plugs 100. The dip coating solution 404 comprises the agent 102 and a bioabsorbable polymer (e.g., Polycaprolactone/Polyglycolic acid) and may also include a solvent. One embodiment of the invention illustrating a non-woven mat that has been dip coated with an agent 102 and polymer is illustrated in FIGS. 4A and 4B. As earlier described, FIG. 4A is an isometric schematic representation of a non-woven fibrous mat the non-woven mat 105 made up of randomly oriented fibers 101. For clarity, FIG. 4B is a section view of the mat 105 depicted in FIG. 4A taken along section line A-A. In each view the dip coating solution 404 is shown encapsulating the outer surfaces of the mat 105. During the solvent removal process, the agent 102 and the polymer are coated uniformly on the fiber 101 surfaces. Alternatively, the agent 102 can be added on the mat 105 surface in the absence of the bioabsorbable polymer. In this embodiment, the agent 102 coating on the non-woven mat 105 may be non-uniform. An isometric schematic representation of a mat 105 having a non-uniform agent 102 coating on the mat 105 surface in illustrated in FIG. 4C.

Figure 4D:
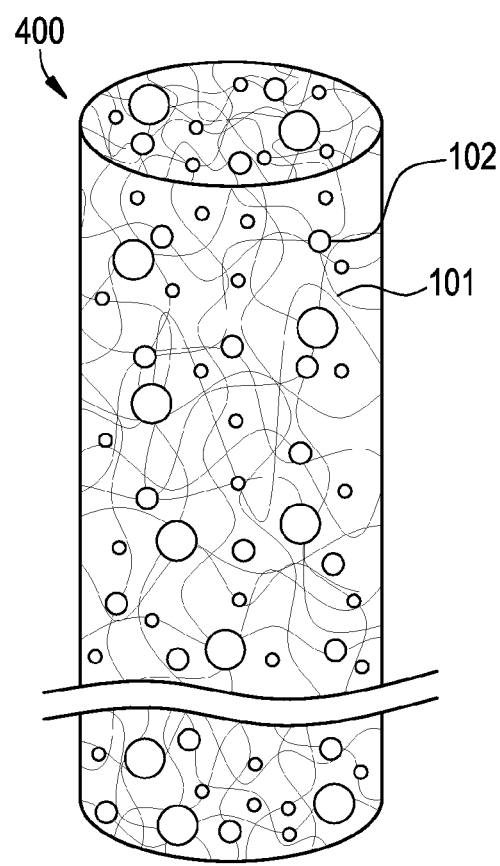
FIG. 4D is a schematic representation of a fibrous antimicrobial plug having agent dispersed between the fiber structure according to one embodiment of the present invention.
Figure 4E:
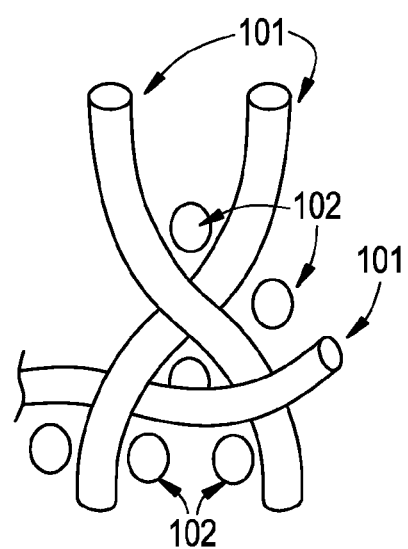
FIG. 4E is a close-up schematic representation of a portion of a fibrous antimicrobial plug having agent dispersed between the fiber structure according to one embodiment of the present invention.

It should be noted that the coating process might also allow the dip coating solution 404 or agent 102, as the case may be, to penetrate the exterior surface of the mat 105 into the interstitial spaces formed between adjacent fibers 101. FIG. 4D is a schematic representation of a plug 101 wherein the agent 102 has penetrated the surface and resides in the interstitial spaces between fibers 101. FIG. 4E is a close up section view of entangled fibers 101 forming the interstitial spaces occupied by agent 102. Although not explicitly depicted, the plug 101 may have agent 102 or solution 404 covering the top and bottoms ends of the cylindrical plug 101. In addition, the coating process may allow some amount of agent or coating solution 404 to cover various side sections of the plug 101.

Figure 5A:
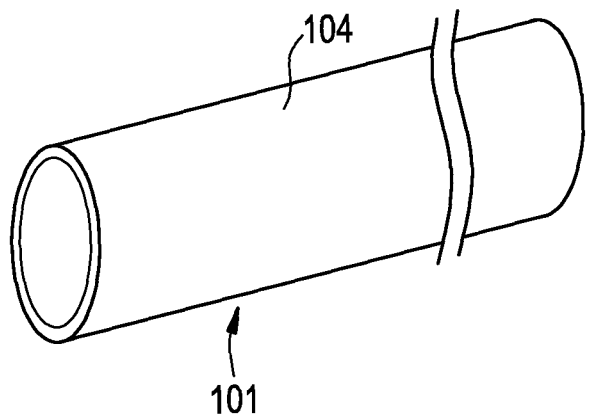
FIG. 5A is a schematic representation of the fiber in the vascular closure plug having a thin coating of agent along the outer surface of the fiber structure according to one embodiment of the present invention.
Figure 5B:
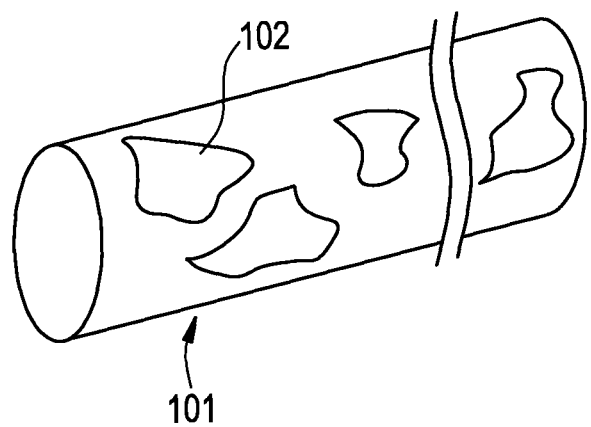
FIG. 5B is a schematic representation of the fiber in the vascular closure plug having a thin coating of agent along a portion of the outer surface of the fiber structure according to one embodiment of the present invention.

FIGS. 5A and 5B are schematic representations of another embodiment of the invention where the extruded filaments 101 are first scoured to remove the spin finish, and the scoured filaments 101 are dip coated with the coating solution 404 (polymer, agent and solvent). During the solvent removal process, the polymer and agent coating 104 disperses uniformly on the filaments 101 as shown in FIG. 5A. These filaments are then crimped, carded, needle punched into a mat 105 and then cut in to plugs 100. Alternatively, the scoured filaments 101 may be dip coated in an agent/solvent solution. During the solvent removal process, the agent 102 remains on the filament 101. The agent may uniformly cover the filament 102, but generally will non-uniformly cover the filament 102 as illustrated in FIG. 5B. These filaments are then crimped, carded, needle punched into a mat 105 and then cut in to plugs 100.

In still another embodiment of the invention, the plugs 100 prepared from the non-woven mat 105 may be covered with a coating after plug formation. This coating may be in the form of a solution or a powder. By way of example a solution of polymer and agent; polymer, agent and solvent; or agent and solvent may be applied to the formed plug 100. In addition, the coating may be applied to the plug 100 in a powdered form, such as through an electrostatic coating process.

Figure 6A:
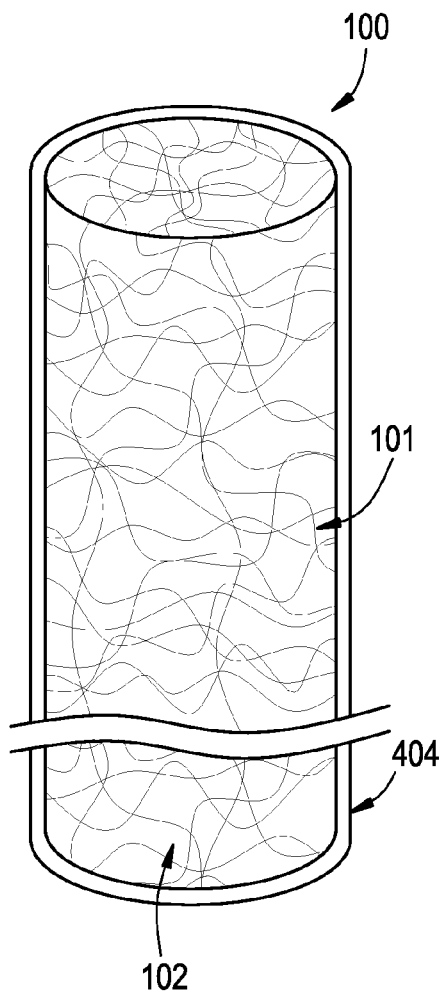
FIG. 6A illustrates a plug that has been dip coated with a polymer/agent/solvent solution according to one embodiment of the present invention.
Figure 6B:
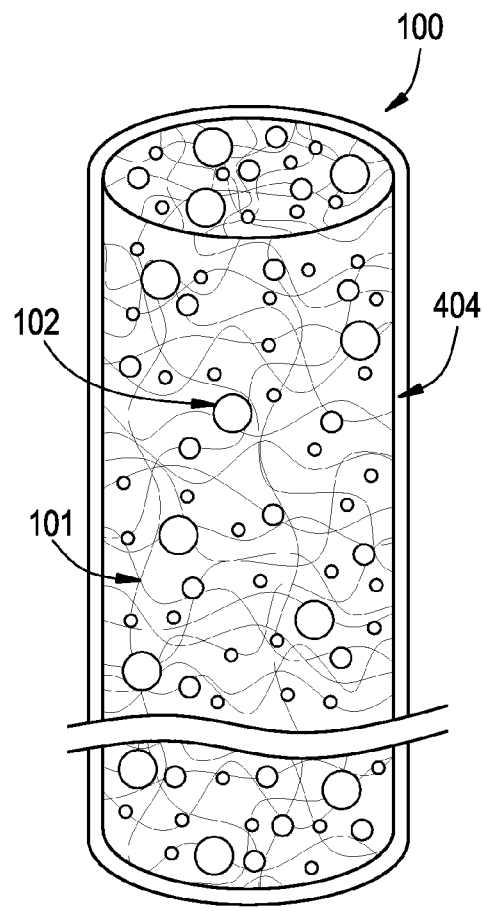
FIG. 6B illustrates a plug having agent occupying the interstitial spaces that has been dip coated with a polymer/agent/solvent solution according to one embodiment of the present invention.

FIGS. 6A-6D are schematic representations illustrating plugs 100 covered after formation with a coating. In particular, FIG. 6A illustrates a plug 101 that has been dip coated with a polymer/agent/solvent solution. When the solvent is removed, the polymer and agent substantially encapsulates the outer surfaces of the plug 100 with a thin coating 404. In addition, the plug 100 may have been originally prepared with the agent occupying the interstitial spaces formed between adjacent randomly oriented fibers 101 before coating. FIG. 6B illustrates a plug 101 having agent occupying the interstitial spaces that has been dip coated with a polymer/agent/solvent solution.

Alternatively, the plug 100 may be dip coated with an agent/solvent solution. When the solvent is removed, the agent 102 may non-uniformly cover the outer surfaces of the plug 100. FIG. 6C is a schematic representation illustrating a plug 100 covered by a non-uniform coating of agent 102 according to one embodiment of the present invention. In addition, the plug 100 may have been originally prepared with the agent 102 occupying the interstitial spaces formed between adjacent randomly oriented fibers 101 before coating. FIG. 6D illustrates a plug 101 having agent occupying the interstitial spaces that has been dip coated with an agent/solvent solution.

There are several alternative methods that can be used to have the agent either dispersed within the fiber matrix or on the fiber surface to provide the antimicrobial properties.

The components of the porous closure device have therapeutic aentsl and polymer coating combinations that are used to deliver the various agents and drugs, i.e. therapeutic and/or pharmaceutical agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)I-$I_b III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), nonsteroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin; angiotensin receptor blocker; nitric oxide donors; anti-sense oligionucleotides and combinations thereof; cell cycle inhibitors, mTOR inhibitors, and growth factor signal transduction kinase inhibitors.

The closure device can be made from biodegradable or bioabsorbable polymer compositions. The type of polymers used can degrade via different mechanisms such as bulk or surface erosion. Bulk erodible polymers include aliphatic polyesters such poly(lactic acid); poly(glycolic acid); poly(caprolactone); poly(p-dioxanone) and poly(trimethylene carbonate); and their copolymers and blends. Other polymers can include amino acid derived polymers; phosphorous containing polymers [e.g., poly(phosphoesters)] and poly(ester amide). Surface erodible polymers include polyanhydrides and polyorthoesters. The closure device can be made from combinations of bulk and surface erodible polymers to control the degradation mechanism of the stent. The selection of the polymers will determine the absorption of that can be very short (few weeks) and long (weeks to months).

The bioabsorbable compositions to prepare the closure device will also include drug and other agents such as antibacterial materials. The drug or agent will release by diffusion and during degradation of the closure device. The porous structure to prepare vascular closure device can be fabricated either by melt or solvent processing.

The medical devices described herein are generally implantable medical devices, including but not limited to mono and multifilament sutures, surgical meshes such as hernia repair mesh, hernia plugs, brachy seed spacers, suture clips, suture anchors, adhesion prevention meshes and films, and suture knot clips. Also included are implantable medical devices that are absorbable and non-absorbable. An absorbable polymer is defined as a polymer that, when exposed to physiological conditions, will degrade and be absorbed by the body over a period of time. Absorbable medical devices typically are formed from generally known, conventional absorbable polymers including, but not limited to, glycolide, lactide, co-polymers of glycolide, or mixtures of polymers, such as polydioxanone, polycaprolactone and equivalents thereof. Examples of absorbable medical device include mono and multifilament sutures. The multifilament suture includes sutures wherein a plurality of filaments is formed into a braided structure. Examples of non-absorbable medical devices include mono and multifilament sutures, surgical meshes such as hernia repair mesh, hernia plugs and brachy seed spacers, which may be polymeric or nonpolymeric.

Suitable antimicrobial agents may be selected from, but are not limited to, halogenated 5 hydroxyl ethers, acyloxydiphenyl ethers, or combinations thereof. In particular, the antimicrobial agent may be a halogenated 2-hydroxy diphenyl ether and/or a halogenated 2-acyloxy diphenyl ether, as described in U.S. Pat. No. 3,629,477.

Antimicrobial activity similar to that of the halogen-o-hydroxy-diphenyl ethers is also attained using the O-acyl derivatives thereof which partially or completely hydrolyze under the conditions for use in practice. The esters of acetic acid, chloroacetic acid, methyl or dimethyl carbamic acid, benzoic acid, chlorobenzoic acid, methylsulfonic acid and chloromethylsulfonic acid are particularly suitable.

One particularly preferred antimicrobial agent within the scope of the above formula is 2,4,4'-trichloro-2'-hydroxy-diphenyl ether, commonly referred to as triclosan (manufactured by Ciba Geigy under the trade name Irgasan DP300 or Irgacare MP). Triclosan is a broad-spectrum antimicrobial agent that has been used in a variety of products, and is effective against a number of organisms commonly associated with SSIs. Such microorganisms include, but are not limited to, genus *Staphylococcus, Staphylococcus epidermidis, Staphylococcus aureus*, methicillin-resistant *Staphylococcus epidermidis*, methicillin-resistant *Staphylococcus aureus*, and combinations thereof.

It is advantageous to use a coating composition as a vehicle for delivering the antimicrobial agent to the surface of the device where such coating already is used conventionally in the manufacture of the device, such as, for example, absorbable and nonabsorbable vascular closure plug. Examples of medical devices, as well as coatings that may be applied thereto, may be found in U.S. Pat. Nos. 4,201,216, 4,027,676, 4,105,034, 4,126,221, 4,185,637, 3,839,297, 6,260,699, 5,230,424, 5,555,976, 5,868,244, 5,972,008 and WO 2004/032704 A2, each of which is hereby incorporated herein in its entirety. As disclosed in U.S. Pat. No. 4,201,216, the coating composition may include a film-forming polymer and a substantially water-insoluble salt of a C6 or higher fatty acid. As another example, an absorbable coating composition that may be used for an absorbable medical device may include poly(alkylene oxylates) wherein the alkylene moieties are derived from C6 or mixtures of C4 to C12 diols, which is applied to a medical device from a solvent solution, as disclosed in U.S. Pat. No. 4,105,034. The coating compositions of the present invention may include a polymer or co-polymer, which may include lactide and glycolide, as a binding agent. The compositions may also include calcium stearate, as a lubricant, and an antimicrobial agent. Medical devices not conventionally employing a coating in the manufacturing process, however, also may be coated with a composition comprising an antimicrobial agent. The coating may be applied to the device by, for example, dip coating, spray coating, suspended drop coating, or any other conventional coating means.

Microorganisms of the genus *Staphylococcus* are the most prevalent of all of the organisms associated with device-related surgical site infection. *S. aureus* and *S. epidermidis* are commonly present on patients' skin and as such are introduced easily into wounds. One of the most efficacious antimicrobial agents against *Staphylococcus* is 2,4,4'-trichloro-2' hydroxydiphenyl ether. This compound has a minimum inhibitory concentration (MIC) against *S. aureus* of 0.01 ppm, as measured in a suitable growth medium and as described by Bhargava, H. et al in the American Journal of Infection Control, June 1996, pages 209-218. The MIC for a particular antimicrobial agent and a particular microorganism is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrase "an amount sufficient to substantially inhibit bacterial colonization" as used herein is defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the anti-microbial agent diffuses through the medium, and as long as the concentration of the antimicrobial agent is above the minimum inhibitory concentration (MIC), none of the susceptible organism will grow on or around the disk for some distance. This distance is called a zone of inhibition. Assuming the antimicrobial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

Alternatively, the concentration of triclosan on the surface of a medical device such as a coated vascular closure plug may be greater than about 0.01 ppm (wt./wt. coating) or between about 30 ppm to 5,000 ppm (wt./wt. plug). The concentration of triclosan on the surface of the delivery system or package or containment compartment may be between about 5 ppm to 5,000 ppm (wt./wt. package or compartment). For other particular applications, however, higher amounts of antimicrobial agent may be useful and should be considered well within the scope of the present invention.

In accordance with various methods of the present invention, a package and containment compartment that are initially substantially free of an antimicrobial agent, i.e., no antimicrobial agent is intended to be present on the package or containment compartment surfaces, may be provided. A medical device, which has an antimicrobial agent disposed thereon, is positioned within the package or containment compartment. Subsequently, the package, the containment compartment if utilized and the medical device are subjected to time, temperature and pressure conditions sufficient to vapor transfer a portion of the antimicrobial agent from the medical device to the package and/or the containment compartment.

The rate of transfer of an antimicrobial agent such as triclosan from the medical device to the package and/or containment compartment is substantially dependent upon the time, temperature and pressure conditions under which the package with the containment compartment and the medical device is processed, stored and handled. For example, triclosan is capable of transferring from a vascular plug to a containment compartment (in a closed vial at atmospheric pressure) when the temperature is maintained at 55° C. over a period of time. The conditions to effectively vapor transfer an antimicrobial agent such as triclosan include a closed environment, atmospheric pressure, a temperature of greater than 40° C., for a period of time ranging from 4 to 8 hours. Also included are any combinations of pressure and temperature to render a partial pressure for the antimicrobial agent that is the same as the partial pressure rendered under the conditions described above, in combination with a period of time sufficient to render an effective amount or concentration of the antimicrobial agent on the package and/or containment compartment, i.e., the minimum inhibitory concentration (MIC) or greater. Specifically, it is known to one of ordinary skill that if the pressure is reduced, the temperature may be reduced to effect the same partial pressure. Alternatively, if the pressure is reduced, and the temperature is held constant, the time required to render an effective amount or concentration of the antimicrobial agent on the package and/or containment compartment may be shortened. While a portion of the antimicrobial agent is transferred to the package and/or containment compartment during this process, a second portion is retained on the surface of the medical device. Accordingly, after the transfer, the medical device and the package and/or the containment compartment contain the antimicrobial agent in an amount effective to substantially inhibit bacterial colonization thereon and thereabout.

Example 1

Coating experiments were conducted using a PGA plug to evaluate the effect of triclosan as an antibacterial agent for vascular closure devices. Each plug was hand dipped in a coating solution for 10 seconds and then air dried at ambient temperature for 2 h. Table I summarizes the coating compositions. Samples 1 to 6 were packaged in universal folders containing vapor hole without tyvek patches, and samples 7 and 8 were packaged in universal folders containing the vapor hole and dosed tyvek patches. All the samples were sterilized by ethylene oxide. The sterilized plug samples were then cut into two pieces and tested against two strains of bacteria namely, *Staphylococcus aureus* and *Escherichia coli*, to determine zone of inhibition (ZOI). Table I summarizes the results from this test. The ZOI results show that all plug samples provide anti bacterial effects for *S. aureus* bacteria exceeding 40 mm; and different levels of inhibition (from 7.7 mm to greater than 40 mm) for *E. coli* bacteria.

TABLE I

Summary of coating compositions and zone of inhibition for PGA plugs

| Sample ID | Substrate | Sample Type | Coating Composition | Zone of Inhibition (mm) S. aureus | Zone of Inhibition (mm) E. Coli |
|---|---|---|---|---|---|
| 1 | PGA plug | Control | No Coating | 0 | 0 |
| 2 | PGA plug | Coated | 2% w/w triclosan in ethyl acetate (no polymer) | >40 | 7.7 |
| 3 | PGA plug | Coated | 2% w/w triclosan and 5% w/w PLGA 65/35 in ethyl acetate | >40 | 14.5 |
| 4 | PGA plug | Coated | 2% w/w triclosan and 1% w/w PLGA 65/35 in ethyl acetate | >40 | 14.5 |
| 5 | PGA plug | Coated | 2% w/w triclosan and 5% w/w PCL/PGA 90/10 in ethyl acetate | >40 | >40 |
| 6 | PGA plug | Coated | 2% w/w triclosan and 1% w/w PCL/PGA 90/10 in ethyl acetate | >40 | >40 |
| 7 | PGA plug | Vapor | 8 mg triclosan in tyvek patch by vapor deposition (no polymer) | >40 | 14.5 |

TABLE I-continued

Summary of coating compositions and zone of inhibition for PGA plugs

| Sample ID | Substrate | Sample Type | Coating Composition | Zone of Inhibition (mm) S. aureus | Zone of Inhibition (mm) E. Coli |
|---|---|---|---|---|---|
| 8 | PGA plug | Vapor | 4 mg triclosan in tyvek patch by vapor deposition (no polymer) | >40 | 14.5 |

Material Characteristics

Accordingly, in one exemplary embodiment, a vascular closure device may be fabricated from a material such as a polymeric material including non-crosslinked thermoplastics, cross-linked thermosets, composites and blends thereof. There are typically three different forms in which a polymer may display the mechanical properties associated with solids; namely, as a crystalline structure, as a semi-crystalline structure and/or as an amorphous structure. All polymers are not able to fully crystallize, as a high degree of molecular regularity within the polymer chains is essential for crystallization to occur. Even in polymers that do crystallize, the degree of crystallinity is generally less than one hundred percent. Within the continuum between fully crystalline and amorphous structures, there are two thermal transitions possible; namely, the crystal-liquid transition (i.e. melting point temperature, $T_m$) and the glass-liquid transition (i.e. glass transition temperature, $T_g$). In the temperature range between these two transitions there may be a mixture of orderly arranged crystals and chaotic amorphous polymer domains.

Molecular orientation is important as it primarily influences bulk polymer properties and therefore will have a strong effect on the final properties that are essential for different material applications. Physical and mechanical properties such as permeability, wear, refractive index, absorption, degradation rates, tensile strength, yield stress, tear strength, modulus and elongation at break are some of the properties that will be influenced by orientation. Orientation is not always favorable as it promotes anisotropic behavior. Orientation may occur in several directions such as uniaxial, biaxial and multiaxial. It may be induced by drawing, rolling, calendaring, spinning, blowing, and any other suitable process, and is present in systems including fibers, films, tubes, bottles, molded and extruded articles, coatings, and composites. When a polymeric material is processed, there will be preferential orientation in a specific direction. Usually it is in the direction in which the process is conducted and is called the machine direction (MD). Many of the products are purposely oriented to provide improved properties in a particular direction. If a product is melt processed, it will have some degree of preferential orientation. In case of solvent processed materials, orientation may be induced during processing by methods such as shearing the polymer solution followed by immediate precipitation or quenching to the desired geometry in order to lock in the orientation during the shearing process. Alternately, if the polymers have rigid rod like chemical structure then it will orient during processing due to the liquid crystalline morphology in the polymer solution.

The orientation state will depend on the type of deformation and the type of polymer. Even though a material is highly deformed or drawn, it is not necessary to impart high levels of orientation as the polymer chains may relax back to their original state. This generally occurs in polymers that are very flexible at the draw temperature. Therefore, several factors may influence the state of orientation in a given polymer system, including rate of deformation for example, strain rate, shear rate, frequency, and the like, amount of deformation or draw ratio, temperature, molecular weight and its distribution, chain configuration for example, stereoregularity, geometrical isomers, and the like, chain architecture, for example, linear, branched, cross-linked, dendritic and the like, chain stiffness, for example, flexible, rigid, semi-rigid, and the like, polymer blends, copolymer types, for example, random, block, alternating, and the like, and the presence of additives, for example, plasticizers, hard and soft fillers, long and short fibers, therapeutic agents and the like.

Since polymers consist of two phases; namely, crystalline and amorphous, the effect of orientation will differ for these phases, and therefore the final orientation may not be the same for these two phases in a semi-crystalline polymer system. This is because the flexible amorphous chains will respond differently to the deformation and the loading conditions than the hard crystalline phase.

Different phases may be formed after inducing orientation and its behavior depends on the chemistry of the polymer backbone. A homogenous state such as a completely amorphous material would have a single orientation behavior. However, in polymers that are semi-crystalline, block copolymers or composites, for example, fiber reinforced, filled systems and liquid crystals, the orientation behavior needs to be described by more than one parameter. Orientation behavior, in general, is directly proportional to the material structure and orientation conditions. There are several common levels of structure that exist in a polymeric system, such as crystalline unit cell, lamellar thickness, domain size, spherulitic structures, oriented superstructures, phase separated domains in polymer blends and the like.

Processes

According to the systems and methods of the present invention, a vascular closure device comprised of polymeric, bioabsorbable materials may be made by any of a variety of processes. The processes used to prepare the antimicrobial vascular closure device are preferably low temperature processes in order to minimize the degradation of the agents that are unstable at high temperatures and are incorporated into the matrix of bioabsorbable polymeric materials comprising the device. Processing methods may comprise forming the device from bioabsorbable polymeric materials via low temperature, solution-based processes using solvents as by, for example, fiber spinning, including dry and wet spinning, electrostatic fiber spinning, co-mingled fibers, solvent extraction, coating, wire-coating, hollow fiber and membrane spinning, spinning disk (thin films with uniform thickness), ink-jet printing (three dimensional printing and the like), lyophilization, extrusion and co-extrusion, supercritical fluids, solvent cast films, or solvent cast tubes. Alternately, the vascular closure devices may also be prepared by more conventional polymer processing methods in melt condition for drugs or agents that are stable at high temperature as by, for example, fiber spinning, extrusion, co-extrusion, injection molding, blow molding, pultrusion and compression molding. Alternately, the agents may also be incorporated in the device by diffusion through the polymer matrix. This may be achieved by several methods such as swelling the device in a agent-enriched solution followed by high-pressure diffusion or by swelling and diffusing the agent in the device using supercritical fluids. Alternately, the drugs or agents may be sprayed, dipped, or coated onto the device after formation thereof from the bioabsorbable polymers. In either case, the polymer matrix, and drug or agent blend when provided, is then converted into a structure such as fibers, films, foams, discs/rings or tubes, for example, that is thereafter further manipulated into various geometries or configurations as desired.

Different processes may provide different structures, geometries or configurations to the bioabsorbable polymer being processed. For example, tubes processed from rigid polymers tend to be very stiff, but may be very flexible when processed via electrostatic processing or lyophilization. In the former case, the tubes are solid, whereas in the latter case, the tubes are porous. Other processes provide additional geometries and structures that may include fibers, microfibers, thin and thick films, discs, foams, microspheres and even more intricate geometries or configurations. The differences in structures, geometries or configurations provided by the different processes are useful for preparing different devices with desired dimensions, strengths, agent or drug delivery and visualization characteristics.

In the case of a vascular closure device comprised of bioabsorbable polymeric materials formed by supercritical fluids, such as supercritical carbon dioxide, the supercritical fluids are used to lower processing temperatures during extrusion, molding or otherwise conventional processing techniques. Different structures, such as fibers, tubes, films, or foams, may be formed using the supercritical fluids, whereby the lower temperature processing that accompanies the supercritical fluids tends to minimize degradation of the agents or drugs incorporated into the structures formed.

Solvent Processing

In the case of a vascular closure device comprised of bioabsorbable polymeric materials formed from solution, the viscosity of the polymer solution will determine the processing method used to prepare the devices. Viscosity of the polymer solutions will, in turn, depend on factors such as the molecular weight of the polymer, polymer concentration, and the solvent used to prepare the solutions, processing temperatures and shear rates.

Another method to prepare tubes or fibers from polymer solutions, for example in the range from about 1 percent to 50 percent (wt/wt), is to extrude the solutions using an extruder with a tubular or rod die. During extrusion, the viscosity of the solution may be raised by gradual removal or multi-stage de-volatilization of solvent from vents using, for example, vacuum pumps. Twin screw or vented screw extruders may be used for this purpose. Residual solvent may be further removed at temperatures and conditions that will not degrade the drug. The polymer solutions may also comprise antibacterial agent and other additives such as plasticizers, other polymers and the like.

All the solvent processed devices may be prepared in different shapes, geometries and configurations. For example, the tube may be co-extruded and/or wire coated. Other processing methodologies that are known in the art may be utilized.

Melt Processing

Vascular closure devices may also be prepared by more conventional polymer processing methods in melt condition for drugs or agents that are stable at high temperature. Polymer compounding may be achieved by using twin-screw extruders with different screw elements to achieve desired mixing and dispersion. There are also feeders to add additives during the compounding process to from multi-component blends or composites. These additives may include pellets, powders of different sizes, short fibers or liquids. Polymer and antibacterial agent, for example, 1 percent to about 50 percent (wt/wt) may be melt-compounded using a twin-screw extruder at low temperatures under low shear conditions. The compounded material may be pelletized and extruded into a tube, fiber or other desired geometry using a single screw extruder. Other additives such as plasticizers and other polymers may also be added to the polymer formulation during the compounding step.

In the case of a vascular device comprised of bioabsorbable materials formed by co-extrusion, different bioabsorbable polymeric materials may be used whereby the different polymer tubes or fibers are extruded generally at the same time to form an outer layer for tubes or sheaths in case of fibers, and a inner layer for tubes or core in case of fibers. Bioabsorbable polymeric materials having low melting points are extruded to form the sheath or outside surface, and these low melting point materials will incorporate the drugs or other bio-active agents for eventual delivery to the patient. Materials and their blends having higher melting points are extruded to form the core or inside surface that is surrounded by the sheath. During processing, the temperatures for extruding the low melting point drug comprising materials, for example, polycaprolactone, polydioxanone, and their copolymers and blends may be as low as 60 degrees C. to 100 degrees C. Further, because the drugs or other bio-active agents added to the devices made by this co-extrusion method tend to be coated onto the device after the device has been extruded, the drugs or agents are not exposed to the high temperatures associated with such methods. Degradation of the drugs during processing is therefore minimized.

In the case of a vascular closure device comprised of bioabsorbable polymeric materials formed by co-mingled fibers, different bioabsorbable polymeric materials may also be used. Contrary to the co-extrusion techniques described above, the co-mingled fibers technique requires that each fiber be separately extruded and then later combined to form a device of a desired geometry. Alternately, different fibers may also be extruded using the same spin pack but from different spinning holes thereby combining them in one step. The different bioabsorbable polymeric materials include a first fiber having a low temperature melting point into which a drug is incorporated, and a second fiber having a higher temperature melting point.

There are several different morphological variations that may occur during melt or solution processing bioabsorbable materials. When semi-crystalline polymers are processed from solution, since the solvent evaporates gradually, the polymers may get sufficient time to re-crystallize before it is completely dry. It will also allow time for phase separation to occur in case of multi-component blend systems. These changes are driven by well-known theories of thermodynamics of polymer crystallization and phase separation. In order to prepare, for example, amorphous tubes or films or fibers from solution, it may be necessary to remove the solvent in a relatively short time so that kinetics will prevent crystallization and phase separation from occurring. For example, when the PLGA fibers are prepared from dioxane solutions, it may be necessary to remove the solvent in a relatively short time, for example, a few minutes to hours at low temperatures, for example, below 60 degrees C., after the fiber forming process to obtain an almost amorphous material. If the solvent removal process is carried out over a long period of time, for example, 6 to 10 h, at elevated temperatures, for example, 60 degrees C., then PLGA may begin to crystallize (up to 10 to 20 percent crystallinity). In case of polymer blends, it is preferred to have an amorphous system to achieve good compatibility between the amorphous phases of the polymers so that the physical properties are not adversely affected. When the polymer solutions are precipitated or coagulated, the resulting structure will be almost amorphous (1 to 5 percent crystallinity), as the solvent removal process is very fast thereby not allowing the polymer to crystallize.

In case of melt processed materials, the tubes or films or fibers are quenched immediately after exiting the extrusion die. Therefore, the polymers, in general, do not crystallize if the quenched temperature is below the glass transition temperature of the materials. In case of PGA or PLGA, the extruded fiber or tubes have very low levels of crystallinity (1 to 5 percent). This also makes it favorable when polymer blends are prepared from this process. Annealing the materials between the glass transition and melt temperatures for a given period of time will increase the amount of crystallinity. For example, PLGA fibers or tubes may be annealed at 110 degrees C. for 3 to 10 h by mounting them over a mandrel under tension to prevent any shrinkage or buckling. The amount of crystallinity will increase from about 0 percent to about 35 to 45 percent. Accordingly, this way the properties may be altered to achieve the desired morphology and physical properties.

These morphological variations in the precursor material (fibers, tubes, films, etc) will dictate to some extent the performance of the devices prepared from these materials. Amorphous materials will absorb faster, have higher toughness values, will physically age, and may not have sufficient dimensional stability compared to crystalline material. In contrast, crystalline material may not form compatible blends, will take a longer time to absorb, are stiffer with lower toughness values, and may have superior physical device properties such as low creep, higher strength, etc. For example, a material that is mechanically tested from a quenched state (higher amorphous form) and a slow cooled state (higher crystalline form) will provide a ductile high deformation behavior and a brittle behavior, respectively. This behavior is from the differences in the crystallinity and morphological features driven by different thermal treatments and histories. The morphological structure of a device surface may be modified by applying energy treatment (e.g., heat). For example, an amorphous surface morphology can be converted to a crystalline surface morphology by annealing it under different conditions (temperature/time). This may result in the formation of a crystalline skin or layer on the device that may provide several benefits such as agent elution control and surface toughness to prevent crack formation and propagation. Therefore, it is important to balance the structure—property—processing relationship for the materials that are used to prepare the devices to obtain optimum performance.

The implantable medical devices of the current invention may be prepared from pure polymers, blends, and composites and may be used to prepare agent or drug-loaded vascular closure devices. The precursor material may be a fiber or a tube or a film that is prepared by any of the processes described above. The precursor material may be used as prepared or can be modified by quenching, annealing, orienting or relaxing them under different conditions. Alternately, the device may be used as prepared or may be modified by quenching, annealing, orienting or relaxing them under different conditions.

Mechanical Orientation

Orientation may be imparted to fibers, tubes, films or other geometries that are loaded or coated with agents or drugs in the range from about 1 to 50 percent. For example, drug loaded PGA tubes prepared by any of the above-mentioned processes may be oriented at about 70 degrees C. to different amounts (for example, 50 percent to 300 percent) at different draw rates (for example, 100 mm/min to 1000 mm/min). The conditions to draw the material is important to prevent excessive fibrillation and void formation that may occur due to the presence of drug. If the draw temperature is increased to a higher value (for example, 90 degrees C.), then the orientation may not be retained as the temperature of orientation is much higher than the glass transition temperature of PGA (about 45 degrees C.) and would cause relaxation of the polymer chains upon cooling.

Other methods of orienting the materials may include multi-stage drawing processes in which the material or device may be drawn at different draw rates at different temperatures before or after intermediate controlled annealing and relaxation steps. This method allows increasing the total draw ratio for a given material that is not otherwise possible in one-step drawing due to limitations of the material to withstand high draw ratio. These steps of orientation, annealing and relaxation will improve the overall strength and toughness of the material.

Polymeric Materials

Polymeric materials may be broadly classified as synthetic, natural and/or blends thereof. Within these broad classes, the materials may be defined as biostable or biodegradable. Examples of biostable polymers include polyolefins, polyamides, polyesters, fluoropolymers, and acrylics. Examples of natural polymers include polysaccharides and proteins.

Bioabsorobable and/or biodegradable polymers consist of bulk and surface erodible materials. Surface erosion polymers are typically hydrophobic with water labile linkages. Hydrolysis tends to occur fast on the surface of such surface erosion polymers with no water penetration in bulk. The initial strength of such surface erosion polymers tends to be low however, and often such surface erosion polymers are not readily available commercially. Nevertheless, examples of surface erosion polymers include polyanhydrides such as poly(carboxyphenoxy hexane-sebacic acid), poly(fumaric acid-sebacic acid), poly(carboxyphenoxy hexane-sebacic acid), poly(imide-sebacic acid)(50-50), poly(imide-carboxyphenoxy hexane) (33-67), and polyorthoesters (diketene acetal based polymers).

Bulk erosion polymers, on the other hand, are typically hydrophilic with water labile linkages. Hydrolysis of bulk erosion polymers tends to occur at more uniform rates across the polymer matrix of the device. Bulk erosion polymers exhibit superior initial strength and are readily available commercially.

Examples of bulk erosion polymers include poly($\alpha$-hydroxy esters) such as poly(lactic acid), poly(glycolic acid), poly(caprolactone), poly(p-dioxanone), poly(trimethylene carbonate), poly(oxaesters), poly(oxaamides), and their copolymers and blends. Some commercially readily available bulk erosion polymers and their commonly associated medical applications include poly(dioxanone) [PDS® suture available from Ethicon, Inc., Somerville, N.J.], poly(glycolide) [Dexon® sutures available from United States Surgical Corporation, North Haven, Conn.], poly(lactide)-PLLA [bone repair], poly(lactide/glycolide) [Vicryl® (10/90) and Panacryl® (95/5) sutures available from Ethicon, Inc., Somerville, N.J.], poly(glycolide/caprolactone (75/25) [Monocryl® sutures available from Ethicon, Inc., Somerville, N.J.], and poly(glycolide/trimethylene carbonate) [Maxon® sutures available from United States Surgical Corporation, North Haven, Conn.].

Other bulk erosion polymers are tyrosine derived poly amino acid [examples: poly(DTH carbonates), poly(arylates), and poly(imino-carbonates)], phosphorous containing polymers [examples: poly(phosphoesters) and poly(phosphazenes)], poly(ethylene glycol) [PEG] based block co-polymers [PEG-PLA, PEG-poly(propylene glycol), PEG-poly (butylene terephthalate)], poly(α-malic acid), poly(ester amide), and polyalkanoates [examples: poly(hydroxybutyrate (HB) and poly(hydroxyvalerate) (HV) co-polymers].

Of course, the devices may be made from combinations of surface and bulk erosion polymers in order to achieve desired physical properties and to control the degradation mechanism. For example, two or more polymers may be blended in order to achieve desired physical properties and device degradation rate. Alternately, the device may be made from a bulk erosion polymer that is coated with a surface erosion polymer. The drug delivery device may be made from a bulk erosion polymer that is coated with a antibacterial agent containing a surface erosion polymer. For example, the coating may be sufficiently thick that high loads may be achieved, and the bulk erosion polymer may be made sufficiently thick that the mechanical properties of the device are maintained even after all of the drug has been delivered and the surface eroded.

Shape memory polymers may also be used. Shape memory polymers are characterized as phase segregated linear block co-polymers having a hard segment and a soft segment. The hard segment is typically crystalline with a defined melting point, and the soft segment is typically amorphous with a defined glass transition temperature. The transition temperature of the soft segment is substantially less than the transition temperature of the hard segment in shape memory polymers. A shape in the shape memory polymer is memorized in the hard and soft segments of the shape memory polymer by heating and cooling techniques. Shape memory polymers may be biostable and bioabsorbable. Bioabsorbable shape memory polymers are relatively new and comprise thermoplastic and thermoset materials. Shape memory thermoset materials may include poly(caprolactone)dimethylacrylates, and shape memory thermoplastic materials may include poly (caprolactone) as the soft segment and poly(glycolide) as the hard segment.

The selection of the bioabsorbable polymeric material used to comprise the device according to the invention is determined according to many factors including, for example, the desired absorption times and physical properties of the bioabsorbable materials, and the geometry of the drug delivery device.

The local delivery of the antibacterial agent/therapeutic agent combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, including stents, stent-grafts and other devices for repairing aneurysms, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any other type of medical device may be coated in some fashion with a drug or drug combination, which enhances treatment over use of the singular use of the device or pharmaceutical agent.

In addition to various medical devices, the coatings on these devices may be used to deliver therapeutic and pharmaceutic agents including, all the compounds described above and anti-proliferative agents, anti-throrombogenic agents, anti-restenotic agents, anti-infective agents, anti-viral agents, anti-bacterial agents, anti-fungal agents, anti-inflammatory agents, cytostatic agents, cytotoxic agents, immunosuppressive agents, anti-microbial agents, anti-calcification agents, anti-encrustation agents, statins, hormones, anti-cancer agents, anti-coagulants, anti-migrating agents and tissue growth promoting agents.

As described herein, various drugs or agents may be incorporated into the medical device by a number of mechanisms, including blending it with the polymeric materials or affixing it to the surface of the device. Different drugs may be utilized as therapeutic agents, including sirolimus, or rapamycin, heparin, everolimus, tacrolimus, paclitaxel, cladribine as well as classes of drugs such as statins. These drugs and/or agents may be hydrophilic, hydrophobic, lipophilic and/or lipophobic.

Rapamycin is a macroyclic triene antibiotic produced by *streptomyces hygroscopicus* as disclosed in U.S. Pat. No. 3,929,992. It has been found that rapamycin inhibits the proliferation of vascular smooth muscle cells in vivo. Accordingly, rapamycin may be utilized in treating intimal smooth muscle cell hyperplasia, restenosis and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

The drugs, agents or compounds described herein may be utilized in combination with any number of medical devices, and in particular, with implantable medical devices such as stents and stent-grafts. Other devices such as vena cava filters and anastomosis devices may be used with coatings having drugs, agents or compounds therein or the devices themselves may be fabricated with polymeric materials that have the drugs contained therein.

Any of the above-described medical devices may be utilized for the local delivery of drugs, agents and/or compounds to other areas, not immediately around the device itself. In order to avoid the potential complications associated with systemic drug delivery, the medical devices of the present invention may be utilized to deliver the agents to areas adjacent to the medical device. For example, a triclosan coated vascular closure plug may deliver the agent to the tissues surrounding the plug. The degree of tissue penetration depends on a number of factors, including the drug, agent or compound, the concentrations of the drug and the release rate of the agent.

The amount of agent incorporated within the device according to the systems and methods of the present invention may range from about 0 to 99 percent (percent weight of the device). The drugs or other agents may be incorporated into the device in different ways. For example, the drugs or other agents may be coated onto the device after the device has been formed, wherein the coating is comprised of bioabsorbable polymers into which the drugs or other agents are incorporated. Alternately, the drugs or other agents may be incorporated into the matrix of bioabsorbable materials comprising the device. The drugs or agents incorporated into the matrix of bioabsorbable polymers may be in an amount the same as, or different than, the amount of drugs or agents provided in the coating techniques discussed earlier if desired. These various techniques of incorporating drugs or other agents into, or onto, the device may also be combined to optimize performance of the device, and to help control the release of the drugs or other agents from the device.

Where the drug or agent is incorporated into the matrix of bioabsorbable polymers comprising the device, for example, the drug or agent will release by diffusion and during degradation of the device. The amount of drug or agent released by diffusion will tend to release for a longer period of time than occurs using coating techniques, and may often more effectively treat local and diffuse conditions thereof. Polymer compositions and their diffusion and absorption characteristics will control agent or drug elution profile for these devices. The release kinetics will be controlled by diffusion and polymer absorption. Initially, most of the agent or drug will be released by diffusion from the device surfaces and bulk and will then gradually transition to release due to polymer absorption. There may be other factors that will also control drug or agent release. If the polymer composition is from the same monomer units (e.g., lactide; glycolide), then the diffusion and absorption characteristics will be more uniform compared to polymers prepared from mixed monomers. Also, if there are layers of different polymers with different drug in each layer, then there will be more controlled release of drug from each layer. There is a possibility of agent or drug present in the device until the polymer fully absorbs thus providing drug release throughout the device life cycle.

The vascular closure device according to the systems and methods of the present invention preferably retains its integrity during the active drug delivery phase of the device. After drug delivery is achieved, the structure of the device ideally disappears as a result of the bioabsorption of the materials comprising the device. The bioabsorbable materials comprising the drug delivery device are preferably biocompatible with the tissue in which the device is implanted such that tissue interaction with the device is minimized even after the device is deployed within the patient. Minimal inflammation of the tissue in which the device is deployed is likewise preferred even as degradation of the bioabsorbable materials of the device occurs. In order to provide multiple drug therapy, enriched or encapsulated drug particles or capsules may be incorporated in the polymer matrix. Some of these actives may provide different therapeutic benefits such as anti-inflammatory, anti-thrombotic; etc.

In accordance with another exemplary embodiment, the vascular closure device described herein may be utilized as antibacterial agents or drug delivery devices wherein the agent is affixed to the surface of the device. Typical material properties for coatings include flexibility, ductility, tackiness, durability, adhesion and cohesion. Biostable and bioabsorbable polymers that exhibit these desired properties include methacrylates, polyurethanes, silicones, poly(vinyl acetate), poly(vinyl alcohol), ethylene vinyl alcohol, poly(vinylidene fluoride), poly(lactic acid), poly(glycolic acid), poly(caprolactone), poly(trimethylene carbonate), poly(dioxanone), polyorthoester, polyanhydrides, polyphosphoester, polyamiinoacids as well as their copolymers and blends thereof.

In addition to the incorporation of therapeutic agents, the surface coatings may also include other additives such as radiopaque constituents, chemical stabilizers for both the coating and/or the therapeutic agent, radioactive agents, tracing agents such as radioisotopes such as tritium (i.e. heavy water) and ferromagnetic particles, and mechanical modifiers such as ceramic microspheres as will be described in greater detail subsequently. Alternatively, entrapped gaps may be created between the surface of the device and the coating and/or within the coating itself. Examples of these gaps include air as well as other gases and the absence of matter (i.e. vacuum environment). These entrapped gaps may be created utilizing any number of known techniques such as the injection of microencapsulated gaseous matter.

As described above, different agents may be utilized as therapeutic agents, including sirolimus, heparin, everolimus, tacrolimus, paclitaxel, cladribine as well as classes of drugs such as statins. These drugs and/or agents may be hydrophilic, hydrophobic, lipophilic and/or lipophobic. The type of agent will play a role in determining the type of polymer. The amount of the drug in the coating may be varied depending on a number of factors including, the storage capacity of the coating, the drug, the concentration of the drug, the elution rate of the drug as well as a number of additional factors. The amount of drug may vary from substantially zero percent to substantially one hundred percent. Typical ranges may be from about less than one percent to about forty percent or higher. Drug distribution in the coating may be varied. The one or more drugs may be distributed in a single layer, multiple layers, single layer with a diffusion barrier or any combination thereof.

Different solvents may be used to dissolve the drug/polymer blend to prepare the coating formulations. Some of the solvents may be good or poor solvents based on the desired drug elution profile, drug morphology and drug stability.

There are several ways to coat the device that are disclosed in the prior art. Some of the commonly used methods include spray coating; dip coating; electrostatic coating; fluidized bed coating; and supercritical fluid coatings.

Some of the processes and modifications described herein that may be used will eliminate the need for polymer to hold the agent on the vascular closure device. Device surfaces may be modified to increase the surface area in order to increase agent or drug content and tissue-device interactions. Nanotechnology may be applied to create self-assembled nanomaterials that can contain tissue specific agent/drug containing nanoparticles. Microstructures may be formed on surfaces by microetching in which these nanoparticles may be incorporated. The microstructures may be formed by methods such as laser micromachining, lithography, chemical vapor deposition and chemical etching. Microstructures may be added to the device surface by vapor deposition techniques. Microstructures have also been fabricated on polymers and metals by leveraging the evolution of micro electro-mechanical systems (MEMS) and microfluidics. Examples of nanomaterials include carbon nanotubes and nanoparticles formed by solgel technology. Therapeutic agents may be chemically or physically attached or deposited directly on these surfaces. Combination of these surface modifications may allow agent or drug release at a desired rate. A top-coat of a polymer may be applied to control the initial burst due to immediate exposure of drug in the absence of polymer coating.

As described above, vascular closure devices may contain antimicrobial or therapeutic agents as a coating, e.g. a surface modification. Alternatively, the agents may be incorporated into the device structure, e.g. a bulk modification that may not require a coating. For devices prepared from biostable and/or bioabsorbable polymers, the coating, if used, could be either biostable or bioabsorbable. However, as stated above, no coating may be necessary because the device itself is fabricated from a delivery depot. This embodiment offers a number of advantages. For example, higher concentrations of the therapeutic agent or agents may be achievable such as about >50 percent by weight. In addition, with higher concentrations of therapeutic agent or agents, agent delivery is achievable for greater durations of time.

The sterilization process of the present invention is particularly adapted to the challenges of sterilizing drug coated medical devices. Specifically, the sterilization process is designed to remove all biological contaminants without affecting the drug, agent or compound or the polymeric material comprising the device or the coating.

Medical devices typically are sterilized to render microorganisms located thereon non-viable. In particular, sterile is understood in the field of art to mean a minimum sterility assurance level of $10^{-6}$. Examples of sterilization processes are described in U.S. Pat. Nos. 3,815,315, 3,068,864, 3,767, 362, 5,464, 580, 5,128,101 and 5,868,244, each of which; is incorporated herein in its entirety. Specifically, absorbable medical devices may be sensitive to radiation and heat. Accordingly, it may be desirable to sterilize such devices using conventional sterilant gases or agents, such as, for example, ethylene oxide gas. Upon completion of the sterilization process, the antimicrobial medical device, the delivery system, the package and/or the containment compartment have thereon an amount of the antimicrobial agent effective to substantially inhibit colonization of bacteria on or adjacent the antimicrobial device, the package and/or the containment compartment.

In accordance with one exemplary embodiment, a low temperature sterilization method may be utilized to sterilize the devices of the present invention. The method comprises the steps of positioning at least one packaged, drug coated or drug containing medical device in a sterilization chamber, creating a vacuum in the sterilization chamber, increasing and maintaining the temperature in the sterilization chamber in the range from about twenty-five degrees C. to about forty degrees C. and the relative humidity in the sterilization chamber in the range from about forty percent to about eighty-five percent for a first predetermined period, injecting a sterilization agent at a predetermined concentration into the sterilization chamber and maintaining the temperature in the sterilization chamber in the range from about twenty-five degrees C. to about forty degrees C. and the relative humidity in the range from about forty percent to about eighty-five percent for a second predetermined period, and removing the sterilization agent from the sterilization chamber through a plurality of vacuum and nitrogen washes over a third predetermined period, the temperature in the sterilization chamber being maintained at a temperature in the range from about thirty degrees C. to about forty degrees C.

In accordance with another exemplary embodiment, a low temperature sterilization method may be utilized to sterilize the devices of the present invention. The method comprising the steps of loading the at least one packaged, drug coated medical device in a preconditioning chamber, the preconditioning chamber being maintained at a first predetermined temperature and a first predetermined relative humidity for a first predetermined time period, positioning at least one packaged, drug coated medical device in a sterilization chamber creating a vacuum in the sterilization chamber increasing and maintaining the temperature in the sterilization chamber in the range from about twenty-five degrees C. to about forty degrees C. and the relative humidity in the sterilization chamber in the range from about forty percent to about eighty-five percent for a first predetermined period injecting a sterilization agent at a predetermined concentration into the sterilization chamber and maintaining the temperature in the sterilization chamber in the range from about twenty-five degrees C. to about forty degrees C. and the relative humidity in the range from about forty percent to about eighty-five percent for a second predetermined period, and removing the sterilization agent from the sterilization chamber through a plurality of vacuum and nitrogen washes over a third predetermined period, the temperature in the sterilization chamber being maintained at a temperature in the range from about thirty degrees C. to about forty degrees C.

In each embodiment described above, the sterilization or sterilizing agent may comprise ethylene oxide or any other suitable agent. The nitrogen washes, which serve to remove the ethylene oxide may be replaced with other suitable gases, including any of the noble gases.

Other sterilization methods may also be used, such gamma and electron beam radiations. In these methods the dosage should be low so that agent or drug in the devices is not adversely affected. The dosage may range from about one to four mrad and more preferably below 2 mrad. Radiation sterilized polymers will absorb relatively faster than ethylene oxide sterilized polymers.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. A vascular closure device comprising:
    a preshaped, cylindrical fibrous plug formed prior to delivery from a nonwoven fabric of at least one randomly oriented and entangled fiber, the thickness of the nonwoven fabric ranging from about 0.25 to 2 mm, the basis weight of the nonwoven fabric ranging from about 0.01 to 0.2 g/in$^2$, the at least one randomly oriented fiber having a density from about 120 to about 150 denier and a tenacity from about 3 to about 7 g/denier, the cylindrical fibrous plug being configured for occluding blood flow from a puncture and sealing a wound in a tract of a puncture wound, the fibrous plug having a definite cylindrical shape and volume ex vivo, the randomly oriented fiber comprising at least one polymer; and
    at least one agent, in therapeutic dosage, dispersed in the fiber matrix of the at least one randomly oriented fiber, and configured for controlled elution therefrom, the at least one agent comprises an agent selected from a group consisting of anti-proliferative agents, anti-thrombogenic agents, anti-restenotic agents, anti-viral agents, anti-inflammatory agents, cytostatic agents, immunosuppressive agents, anti-calcification agents, anti-encrustation agents, statins, hormones, anti-cancer agents, anti-coagulants, anti-migratory agents, tissue growth promoting agents, heparin, and combinations thereof.

2. The vascular closure device according to claim 1, wherein the at least one polymer comprises a blend of one or more polymers.

3. The vascular closure device according to claim 1, wherein the at least one polymer comprises a blend of at least one polymer and at least one plasticizer.

4. The vascular closure device according to claim 1, wherein the at least one polymer comprises a bioabsorbable polymer.

* * * * *